United States Patent [19]
Bohuon

[11] 3,957,853
[45] May 18, 1976

[54] METFORMINE SALT OF ACETYLSALICYLIC ACID

[75] Inventor: Odile Bohuon, Paris, France

[73] Assignee: Societe d'Etudes et d'Exploitation de Marques et Brevets S.E.M.S., France

[22] Filed: Sept. 11, 1974

[21] Appl. No.: 505,015

[30] Foreign Application Priority Data
Sept. 19, 1973 France .............................. 73.33647

[52] U.S. Cl. .............................. 260/480; 424/230; 424/233
[51] Int. Cl.² .......................................... C07C 87/20
[58] Field of Search ..................................... 260/480

[56] References Cited
UNITED STATES PATENTS
2,983,750  5/1961  Cotty et al. ......................... 260/480

FOREIGN PATENTS OR APPLICATIONS
883,331  11/1961  United Kingdom ................. 260/480
1,295,304  5/1962  France ..:............................ 260/480

Primary Examiner—James A. Patten
Attorney, Agent, or Firm—Bucknam and Archer

[57] ABSTRACT

The invention provides metformine monoacetylsalicylate as a novel salt having valuable pharmacological properties, particularly for the treatment of glycemia.

1 Claim, No Drawings

METFORMINE SALT OF ACETYLSALICYLIC ACID

The present invention is concerned with a novel salt of metformine, with a process for its preparation, and with compositions containing it.

Metformine and acetylsalicylic acid are both known compounds and each is used pharmaceutically. Belgian Patent 568,513 describes certain acid addition salts of metformine, including the salicylate, the preferred acid salt being metformine hydrochloride.

We have now surprisingly found that metformine acetylsalicylate has properties which are different from those of a mixture of the two constituents of the salt and also from those of metformine hydrochloride and metformine salicylate.

The term "metformine acetylsalicylate" is used herein to refer to the mono-acetylsalicylate of metformine, that is the compound of the formula:

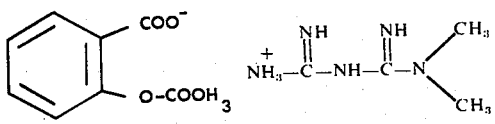

which is formed by the salification of one molecule of metformine base by one molecule of acetysalicylic acid.

Metformine acetylsalicylate is novel and constitutes one aspect of the present invention.

The present invention also comprises a process for the preparation of the novel salt, which comprises reacting substantially equimolar quantities of metformine base and acetylsalicylic acid in an inert solvent, and recovering the salt formed.

The metformine base used should be substantially pure and the purified base is preferably obtained by passing a solution of metformine hydrochloride $(C_4H_{11}N_5.HCl)$ through a column of anionic ion exchange resin. Metformine base is not commercially available because it is unstable, metformine hydrochloride is, however, commercially available. Whilst it is preferred to use equimolar quantities of the base and the acid, it is acceptable to use an excess of up to 10% by weight of the acid without deleteriously affecting the quality of the final product obtained.

The present invention further comprises pharmaceutical compositions comprising metformine acetylsalicylate and an inert, physiologically acceptable carrier. Such compositions may be formulated for oral or parenteral administration and may, if desired, also contain one or more other pharmacologically active compounds.

In order that the invention may be more fully understood, the following examples, the first of which describes the preparation of purified metformine base, are given by way of illustration.

EXAMPLE 1

Preparation of metformine base

In carrying out the process, the following materials were used:

| | |
|---|---|
| metformine hydrochloride | 3000 g (18.1 moles) |
| methanol | 242 l |
| 4% aqueous caustic soda | 100 l |
| demineralised water | 500 l |
| Duolite A101D resin | 25 kg |

An ion exchange column having a capacity of 40 l and a useful height of 1.50 m was used. The following steps were carried out.

i. The resin was placed in the column using some of the demineralised water to form a slurry.

ii. The resin (which was initially in the Cl form) was regenerated by passing the caustic soda solution through the column and then rinsing with a further portion of the demineralised water until the eluate was neutral.

iii. The column was then rinsed with 100 l of methanol containing 2% of water.

iv. A solution of the metformine hydrochloride in 82 l of methanol containing 2% of water, was prepared.

v. This solution was then passed through the column and the eluate was collected; the chloride content of the eluate was determined and was less than or equal to 50 ppm with respect to the solution.

vi. The column was then rinsed with 60 l of methanol containing 2% of water and the rinse eluate was combined with the eluate of step (v). The combined eluates amounted to 142 l of metformine base solution.

vii. The combined eluates were evaporated to dryness under reduced pressure and an external temperature of 40°C which was raised to 60°C at the end of the concentration step in order to eliminate all of the water. The concentration step must be carried out without delay because of the instability of metformine base, which is more marked in solution.

When all the solvent had been eliminated, the metformine was obtained in the form of a clear yellow solid (the yield was approximately 99% of theory). The dry metformine base should also be subjected to salification immediately in view of its instability. It may contain up to 1% of metformine hydrochloride without causing subsequent difficulties.

Methanol was recovered from the distillate of the evaporation step.

viii. The column was then rinsed with 100 l of demineralised water and methanol was recovered from the rinse eluate. At this point, the column was ready for a new cycle of operations commencing with regeneration (step (ii) above).

EXAMPLE 2

Preparation of the salt

18 Moles of freshly prepared metformine base were dissolved, with agitation, in 100 l of acetone contained in a concentration reactor. A small amount of coloured insoluble material (constituting principally of unconverted metformine hydrochloride) was filtered off in the presence of filter aid. 18 Moles of solid acetylsalicylic acid were immediately added to the filtrate. Metformine acetylsalicylate was precipitated; (such precipitation can occur before the acetylsalicyclic acid has completely dissolved but this does not give rise to any subsequent difficulty). Agitation was continued for 15 minutes after the commencement of precipitation.

The mixture of solvent and precipitated metformine acetylsalicylate was then allowed to stand in a cold room. It was then filtered to recover the metformine acetylsalicylate, the latter was washed 4 times with 5 l of acetone and thoroughly drained. Acetone was recovered from the filtrate. The salt was then dried in a ventilated oven at 40°C.

5 Kg or a little more of metformine acetylsalicylate were obtained in the form of a fine white powder, corresponding to an overall yield of about 90% with respect to the initial quantity of metformine hydrochloride used.

Metformine acetylsalicylate has the following characteristics:

It is an anhydrous salt; its m.p. (in capillary tube) is 141°C, whereas that of metformine is 110°C and that of metformine hydrochloride is 225°C; chemical analysis shows that it contains 1 mole of acetylsalicylic acid per mole of metformine; its I.R. spectrum (in liquid petrolatum) does not contain bands at 2500, 2800, 1600 and 1300 cm$^{-1}$ which are characteristic of the free COOH radical of acetylsalicylic acid. Metformine acetylsalicylate is very soluble in water to give substantially neutral solutions.

Pharmacological properties

As a result of pharmacological studies, it has been found that the novel salt has the following properties and characteristics:

a. The LD50 of the novel salt, when tested in Swiss mice, was 2.5 g/kg when orally administered and 1.25 g/kg when intraperitoneally administered.

b. The salt has a hypoglycemic action on alloxanic diabetes in rabbits.

c. The salt is active with respect to plaquette aggregation as shown in the following table which gives the results of tests carried out by the Born method in which the degree of plaquette aggregation in the presence of collagen at 37°C with constant agitation, is determined.

Table

| | Latent period | Intensity | Velocity |
|---|---|---|---|
| Control | 1.20 | 50 | |
| Aspegic* | | | |
| $5\times10^{-3}$ | 2.15 | 19 | 5 |
| $2\times10^{-3}$ | 1.10 | 38 | 13 |
| $10^{-2}$ | curve close to that for $5\times10^{-3}$ | | |
| Control | 1 | 65 | 40 |
| Metformine acetylsalicylate | | | |
| $10^{-3}$ | 1.30 | 1.3 | 5 |
| $4\times10^{-5}$ | 1.15 | 41 | 25 |
| $5\times10^{-3}$ | very flattened curve | | |
| $2\times10^{-3}$ | | 30 | 5 |

*Aspegic = lysine acetylsalicylate

The concentrations in the left hand column are molar concentrations.

d. The salt considerably reduces cholesterolentrained arterial lipid deposits in rabbits receiving a hypercholesterolemic diet.

Therapeutic applications

The novel salt according to the invention is suitable for use in the following indications:

i. Glycemic regulation without risk of hypoglycemic accidents;

ii. Treatment and prevention of vascular complications (micro and macroangiopathy) in diabetic patients;

iii. Prevention and treatment of atheromatous disorders at all levels and, in particular, as an adjuvant to more specific treatments;

iv. Treatment, if desired in association with other salts, of gout and obesity.

For the treatment of diabetic patients, the daily dose of the salt should be chosen in accordance with the degree of glycemia of the patient. In nondiabetic patients, suitable dosages will depend on the illness or condition which is being treated; in general, suitable daily dosages for oral administration are from 50 to 500 mg of the salt. Pharmaceutical compositions containing the novel salt may be formulated for oral or parenteral administration.

What is claimed is:

1. Metformine mono acetylsalicylate.

* * * * *